United States Patent [19]

Culbreth

[11] Patent Number: 5,196,313

[45] Date of Patent: Mar. 23, 1993

[54] METHOD FOR THE EVALUATION OF ANTICOCCIDIAL ACTIVITY OF COMPOUNDS USING 2,3,5-TRIPHENYLTETRAZOLIUM CHLORIDE AND TRYPAN BLUE INDICATORS

[75] Inventor: Walter M. Culbreth, Trenton, N.J.

[73] Assignee: American Cyanamid Company, Stamford, Conn.

[21] Appl. No.: 600,559

[22] Filed: Oct. 16, 1990

Related U.S. Application Data

[63] Continuation of Ser. No. 205,051, Jun. 6, 1988, abandoned, which is a continuation of Ser. No. 909,382, Sep. 19, 1986, abandoned, which is a continuation of Ser. No. 455,382, Jan. 3, 1983, abandoned.

[51] Int. Cl.⁵ .................... C12Q 1/02; C12Q 1/24; C12Q 1/22; C12Q 1/18
[52] U.S. Cl. ............................ 435/32; 435/29; 435/30; 435/31; 435/33
[58] Field of Search ............ 128/760; 514/389; 435/31, 32, 29, 30, 33

[56] References Cited

U.S. PATENT DOCUMENTS 4,199,515 4/1980 Yamagishi et al. .......... 260/345.7 R
4,882,346 11/1989 Driscoll et al. ................ 514/389

OTHER PUBLICATIONS

Mason et al (1968) Exp. Parasitol 23:212–220.
James (1980) Parasitology 80:301–312.
Millard et al (1974) Abstract 166237e Chemical Abstracts.
Weathersby et al (1981) Abstract 33948 Biol Abst 73(5).
Koopman et al (Jul. 1986) Toxicity Screening–in Wastewater Systems. In: Toxicity Testing Using Microorganisms CRC Press, Boca Raton, Fla. pp. 123–125.
Bitton (1983) CRC 13(1) 57–67.

*Primary Examiner*—Christine M. Nucker
*Assistant Examiner*—D. R. Preston
*Attorney, Agent, or Firm*—Peggy A. Climenson

[57] ABSTRACT

A method for the rapid and reliable in vitro determination of the anticoccidial activity of chemotherapeutic agents. The invention involves incubating free-living sporozoites in a nutrient medium in the presence of the anticoccidial agent being assessed and 2,3,5-triphenyltetrazolium chloride. Living sporozoites reduce the above compound to the water-insoluble vivid-red formazan pigment but will not stain with trypan blue; dead sporozoites do not form this red pigment but will stain with trypan blue.

5 Claims, No Drawings

METHOD FOR THE EVALUATION OF ANTICOCCIDIAL ACTIVITY OF COMPOUNDS USING 2,3,5-TRIPHENYLTETRAZOLIUM CHLORIDE AND TRYPAN BLUE INDICATORS

This is a continuation of application Ser. No. 07/205,051 filed Jun. 6, 1988, now abandoned, which is a continuation of application Ser. No. 06/909,382 filed Sep. 19, 1986 now abandoned, which is a continuation of application Ser. No. 06/455,382 filed Jan. 3, 1983 now abandoned.

The invention herein described relates to an in vitro assay which is capable of determining the anticoccidial activity of selected chemotherapeutic agents. The method involves incubating free-living sporozoites in a nutrient medium which contains the anticoccidial agent being evaluated and 2,3,5-triphenyltetrazolium chloride. Living sporozoites reduce this tetrazolium compound to a water-insoluble red formazan pigment and will not stain with trypan blue. In contrast, dead sporozoites do not form the red formazan pigment and will stain with trypan blue. Using this colormetric distinction it is possible by visual observation to determine the relative numbers of living and dead sporozoites and thus evaluate respective chemotherapeutic compounds.

By way of background, coccidiosis is an infestation with, or disease caused by, parasitic protozoans of the order Coccidia. These microorganism parasitize the digestive epithelium of vertebrates. Coccidiosis is an important disease in the area of animal husbandry, particularly with poultry. Annually recurring losses to the poultry industry attributable to chicken coccidiosis are enormous. Control of this sporozoan disease is of considerable importance. Consequently, a large number of compounds are currently being synthesized and evaluated in an attempt to obtain anticoccidials with improved properties for the control of this noxious parasite. In the testing of compounds for anticoccidial activity, wherein free-living sporozoites are employed, there is need for a relatively simple and rapid in vitro assay for evaluating the viability of said sporozoites (a developmental stage of coccidiosis). This would permit the screening of a large number of candidate anticoccidial chemotherapeutic agents.

In light of the foregoing summary of the significance of coccidiosis and some demands and limitations of methods for evaluating anticoccidial agents, an improved method for evaluating antisporozoan activity of chemotherapeutic compounds is highly desirable. An object of this invention is to provide a new and useful method for evaluating the viability of free-living sporozoites of the class Sporozoa. This and further objects are manifest in the following description and particularly delineated in the appended claims.

It has been unexpectedly found that the antisporozoan and especially the anticoccidial activity of candidate compounds can be determined rapidly at a concentration range of about 0.001 to 100 microgram/ml using extracellular sporozoites of *Eimeria tenella* as target organisms.

The free-living sporozoite is an attractive stage of development to exploit for screening of anticoccidial compounds in vitro as they may be obtained readily from oocysts. Drugs may impair the metabolism of sporozoites and affect their viability. Interference with vital metabolic processes may result in defective sporozoites that remain viable but are unable to penetrate and develop normally within the host cell.

The compound 2,3,5-triphenyltetrazolium is represented by structural formula (I):

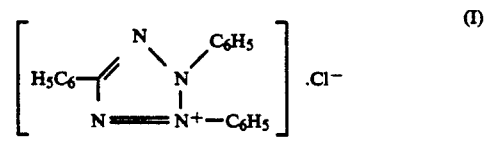

This compound is a colorless, water-soluble compound which is readily reduced by viable cells to form a water-insoluble, vivid deep-red triphenylformazan pigment [Pearse, G. E. 1961. *Histochemistry Theoretical and Applied*. pp. 536–567; Little, Brown and Co., Boston]. Thus, if viable *Eimeria tenella* sporozoites are incubated in a culture medium in the presence of a potential anticoccidial compound wherein the culture medium also contains a small amount of the compound of formula (I), the development of intense red formazan pigment during, or on completion of the incubation period, is indicative of viable cells, whereas dead or metabolically-impaired sporozoites produce no color change.

The dye trypan blue (C.I. 23850) is represented by structural formula (II):

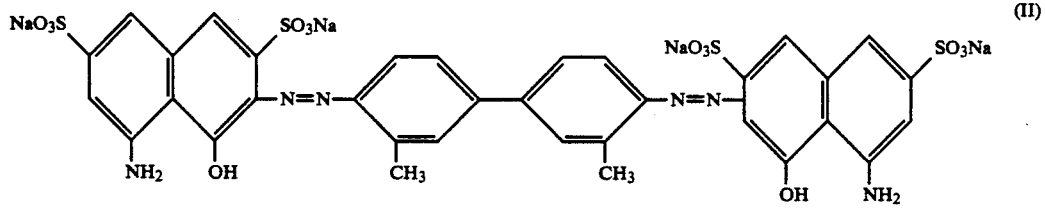

This dye may be used to differentiate between dead and living cells, as it will stain only non-viable cells. Thus, tetrazolium chloride (I) reduction inhibition (TRI) and/or trypan blue (II) uptake (TBU) by sporozoites allows the screening of candidate compounds for anticoccidial activity rapidly and effectively, as by visual observation. It is recognized that the above method may also be used to good advantage for the evaluation and screening of candidate compounds for the control of other protozoan diseases, such as sarcocysta, toxoplasma and especially malaria.

Conveniently, the *Eimeria tenella* sporozoites used in the test are obtained as follows: *E. tenella* sporulated oocysts are isolated on a 0.45μ porosity filter; washed repeatedly with double-distilled water; surface-sterilized by washing with 5% aqueous sodium hypochlorite. The wash cycle is then repeated using sterile, double-distilled water. Oocysts are then suspended in sterile, phosphate-buffered saline (PBS) and are ruptured mechanically, as with a high torque agitator, to release the desired sporocysts.

PBS has the following composition:

| Component | g/l |
|---|---|
| NaCl | 80.00 |
| KCl | 2.00 |
| Na$_2$HPO$_4$ | 21.72 |
| K$_3$PO$_4$ | 2.00 |

The sporocysts are isolated and suspended in "Cold Blood Ringer Solution" containing chicken bile (5%) and trypsin (0.25%). Ringer solution has the following composition:

| Component | g/l |
|---|---|
| NaCl | 6.5 |
| KCl | 0.14 |
| CaCl$_2$ | 0.12 |

The above suspension of sporocysts is incubated at about 41° C. for about 1.5 to 2.0 hours. The freshly-excysted sporozoites are then isolated from the above suspension and washed aseptically with phosphate-buffered saline (PBS). Sporozoites are then suspended in a sterile culture medium prepared by mixing water (870 ml, double-distilled) with Hank's balanced salt solution (10 ml of 10 X) and lactoalbumin hydrocysate; removing 5 ml of the above mixture and replacing same with fetal bovine sera (5 ml); and finally adding a 7.5% sodium bicarbonate solution (1.67 ml) to said mixture. The above suspension also contains 0.05% by weight of 2,3,5-triphenyltetrazolium chloride. It is recognized that other nutrient solutions of similar composition may be substituted for the above culture medium. Hank's balanced salt solution has the following composition:

| Component | g/l |
|---|---|
| CaCl$_2$ | 1.40 |
| KCl | 0.40 |
| KH$_2$PO$_4$ | 0.60 |
| MgCl$_2$.6H$_2$O | 1.00 |
| MgSO$_4$.7H$_2$O | 1.00 |
| NaCl | 80.00 |
| Na$_2$HPO$_4$.7H$_2$O | 0.90$^{10}$ |
| D-Glucose | 10.00 |

The thus-prepared sporozoite suspension is used for the in vitro assay of potential anticoccidials as follows: equal volumes (about 0.1 ml each) of the above sporozoite suspension (containing approximately $5 \times 10^7$ sporozoites/ml) and a solution or dispersion of the candidate compound (at a concentration of about 0.001 to 100 microgram/ml) are mixed and incubated at 41° C. for about 4 to 20 hours in a high humidity environment containing 5% CO$_2$. The samples are visually examined at preselected time intervals during the incubation period and at the completion of experiments. The appearance of the vividred formazan pigment indicates that the sporozoites in the respective samples are viable, since dead or metabolically-impaired sporozoites produce no change. The viability of the sporozoites in these samples, and thus the results obtained by using triphenyltetrazolium chloride (I), can be further supported by mixing a part of the incubated sample with an equal volume of 0.4% trypan blue solution (usually 10 microliters each). The sample is then immediately examined for staining under a phase-contrast microscope at 320X magnification. Viable sporozoites remain unstained. Thus, by using 2,3,5-triphenyltetrazolium chloride (I) or trypan blue (II), and preferably a combination of both as indicators, the in vitro anticoccidial activity of a compound may be quickly and reliably determined using viable sporozoites of Eimeria tenella.

The invention is further illustrated by the examples set forth below. These examples are provided only by way of illustration and are not intended to be limitative of the invention.

EXAMPLE I

Evaluation of the in vitro activity of certain anticoccidial compounds by the method of the invention.

The anticoccidial compounds under evaluation are dissolved or suspended in dimethyl sulfoxide or other appropriate solvent. Appropriate dilutions are made with physiological buffered saline (PBS) solution.

Eimeria tenella oocysts are harvested (Strout, R.G. and Ouellette, C.A. 1973. Eimeria tenella: Screening of chemotherapeutic compounds in cell culture. Exp. Parasitol., 33: 477-485). Next, five to 10 ml of E. tenella sporulated oocysts are added to a millipore filter (0.45$\mu$ porosity) and washed with three 100 ml aliquots of double-distilled water. The external surfaces of the washed oocysts are then sterilized with aqueous sodium hypochlorite solution (5% concentration). The washing cycle is then repeated using sterile distilled water. Sporocysts are obtained by mechanically rupturing the oocysts in sterile PBS using a high torque rotary agitator. The sporocysts are suspended in 10 ml of a 5% solution of fresh chicken bile and 0.25% trypsin prepared with Cold Blood Ringer's Solution and incubated for 1.5 to 2.0 hours in a water bath at 40° C. The freshly-excysted sporozoites are then washed aseptically in PBS and suspended in 15 ml of sterile culture medium (Hank's Balanced Salt Solution) containing 0.05% 2,3,5-triphenyltetrazolium chloride.

The in vitro assay is carried out in 3×5" sterile disposable rigid polystyrene "U" or "V" plates ("Microliter"-Cook Laboratory Products) containing 96 wells. One hundred microliters of the sample to be assayed is added to each well. Next, 100 microliters of the sporozoite suspension (containing approximately $5 \times 10^7$ sporozoites/ml) is added to each sample. The polystyrene plate is covered with a sterile plastic top and incubated at 41° C. for 20 hours in a high-humidity environment containing 5% CO$_2$.

The plates are visually inspected at 2, 4 and 20 hours for the appearance of intense red formazan production indicating that the sporozoites in the respective samples are viable. Dead, or metabolically impaired sporozoites produce no color change.

Trypan blue uptake (TBU) is determined by placing 10 microliters of the respective sporozoite suspension on a glass slide to which 10 microliters of 0.4% trypan blue solution is added. The suspension is then immediately examined under a phase-contrast microscope at 320×magnification. Lack of staining is indicative of the viability of sporozoites. Results of this experiment are presented in Table I.

TABLE 1

Evaluation of the in vitro antisporozoite activity of various compounds.

| Compound | Trypan blue uptake* | Tetrazolium reduction inhibition* |
|---|---|---|
| Arsenobenzene | 0.25 | 1 |
| Carriomycin | 0.50 | 0.50 |
| Clopidol | 0 | 0.50 |
| Decoquinate | 0 | 0.50 |
| Halofuginone | 25 | 25 |
| Lasalocid | 0.125 | 0.50 |
| Methyl bezoquate | 0 | 0.001 |
| Monensin | 0.25 | 0.5 |
| Nitrophenide | 1.0 | 2.0 |
| Robenidine | 5.0 | 5.0 |
| Spiramycin | 5.0 | 0 |
| Oligomycin | 0.06 | 0.06 |
| Salicylanilide | 5 | 5 |
| Nicarbazin | 0 | 5 |

*Minimum effective dose (microgram/ml) after an incubation period of 20 hours at 41° C.

*Maximum level tested for inactive compounds is 100 microgram/ml.

EXAMPLE 2

Tetrazolium reduction inhibition and Trypan blue uptake by *E. tenella* sporozoites incubated for 2, 4 and 20 hours at 41° C. in the presence of certain anticoccidials By the procedure and method of Example 1, *Eimeria tenella* sporozoites are treated with 5 microgram/ml of various anticoccidial agents. Samples are incubated for 20 hours at 41° C. The samples are examined at 2, 4 and 20 hours after the start of the experiment. Results of this experiment are presented in Table II.

TABLE II

Tetrazolium Reduction Inhibition (TRI) and Trypan Blue Stain uptake (TBU) of *Eimeria tenella* sporozoites treated with 5 µg/ml of various anticoccidial agent for 2, 4 and 20 hours at 41° C.

| Anitcoccidial Agent | Incubation Period | | | | | |
|---|---|---|---|---|---|---|
| | 2 Hours | | 4 Hours | | 20 Hours | |
| | TBU | TRI | TBU | TRI | TBU | TRI |
| Carriomycin | ± | − | ± | − | + | + |
| Lasalocid | + | + | + | + | + | + |
| Monensin | ± | − | ± | ± | + | + |
| Methyl nezoquate | − | + | − | + | − | + |
| Nitrophenide | + | + | + | + | + | + |
| Robenidine | − | ± | − | + | + | + |

+ = active
± = marginally active
− = inactive

What is claimed is:

1. A method for evaluating a number of different chemotherapeutic agents for antisporozoan activity, said method consisting essentially of the steps of providing a plurality of different anticoccidial chemotherapeutic agents and for each agent:
   (a) isolating free-living sporozoites from sporulated oocysts of E. tenella,
   (b) suspending the isolated sporozoites in a sterile culture medium containing about 0.05% by weight of 2,3,5-triphenyltetrazolium chloride,
   (c) mixing the sporozoite suspension with about 0.001 to 100 micrograms per milliliter of the chemotherapeutic agent to be evaluated for antisporozoan activity to form a mixture and incubating said mixture in a humid atmosphere of about 5% $CO_2$ at a temperature of about 41° C. for about 4–20 hours;
   (d) macroscopically examining the incubated mixture for the appearance of a red formazan pigment, wherein the red formazan pigment indicates viable sporozoites and no color change indicates dead or metabollically impaired sporozoites, and
   (e) mixing the incubated mixture showing no color change with about 0.4% by weight of trypan blue,
   (f) microscopically examining the mixture of step (e) for blue stained sporozoites, wherein the blue stained sporozoites indicate killed sporozoites.

2. The method according to claim 1, wherein the sporozoite suspension in step (b) is about $5 \times 10^7$ sporozoites per milliliter.

3. The method according to claim 1, wherein in step (c) equal volumes of the sporozoite suspension and the chemotherapeutic agent are mixed.

4. The method according to claim 1, wherein the chemotherapeutic agent of step (c) is in the form of a solution.

5. The method of claim 1, wherein in step (e) equal volumes of trypan blue and the mixture are mixed.

* * * * *